United States Patent
Delgado, III et al.

(10) Patent No.: US 6,323,226 B1
(45) Date of Patent: Nov. 27, 2001

(54) TREATMENT OF HEART DISEASE WITH COX-2 INHIBITORS

(75) Inventors: Reynolds M. Delgado, III; James T. Willerson, both of Houston, TX (US)

(73) Assignees: Texas Heart Institute, Houston; Board of Regents, The University of Texas System, Austin, both of TX (US)

( * ) Notice: Subject to any disclaimer, the term of this patent is extended or adjusted under 35 U.S.C. 154(b) by 0 days.

(21) Appl. No.: 09/690,065

(22) Filed: Oct. 16, 2000

Related U.S. Application Data

(60) Provisional application No. 60/160,440, filed on Oct. 19, 1999.

(51) Int. Cl.[7] .......................... A61K 31/44; A61K 31/42; A61K 31/415; A61K 31/34; A61P 9/04

(52) U.S. Cl. .......................... 514/343; 514/378; 514/403; 514/473

(58) Field of Search .................................. 514/343, 378, 514/403, 473

(56) References Cited

U.S. PATENT DOCUMENTS

| | | | |
|---|---|---|---|
| 5,932,598 | 8/1999 | Talley et al. | 514/341 |
| 6,136,804 | * 10/2000 | Nichtberger | 514/247 |

* cited by examiner

*Primary Examiner*—Raymond Henley, III
(74) *Attorney, Agent, or Firm*—Fulbright & Jaworski, LLP

(57) ABSTRACT

COX-2 selective inhibitors are disclosed as useful in treating or preventing heart disease, and in particular, congestive heart failure.

16 Claims, No Drawings

TREATMENT OF HEART DISEASE WITH COX-2 INHIBITORS

CROSS-REFERENCE TO RELATED APPLICATIONS

This application is a non-provisional application related to U.S. application Ser. No. 60/160,440, filed on Oct. 19, 1999 priority of which is claimed hereunder.

BACKGROUND OF THE INVENTION

The present invention relates to the treatment of heart disease using cyclooxygenase-2 (COX-2) inhibiting drugs. Heart disease can be congenital or caused by an initial precipitating insult. Examples of initial insults include a lack of adequate blood flow, infection, toxins and autoimmune type reactions. Typically cardiac function continues to deteriorate post-initial insult, and heart muscle (myocyte) performance declines.

The term "heart disease" is used in the general sense and includes conditions ranging, for example, from those in which positive inotropic medications are useful to those in which coronary vessel occlusion is predominant, to arrhythmias or cardiotoxicity, such as that which may be observed as a side effect of cardiotoxic drugs, e.g., doxorubicin. In these conditions, it is evident that COX-2 expression and the inflammation that is attendant therewith contribute to the overall disease state.

Congestive heart failure (CHF, cardiac failure) is a form of heart disease in which weakened heart function exists with concommitant edema. Congestive heart failure has many different causes, including narrowing of the arteries supplying blood to the heart muscle (coronary heart disease); prior heart attack (myocardial infarction) resulting in scar tissue large enough or located so to interfere with normal electrocardiac function; high blood pressure; heart valve disease, such as due to past rheumatic fever or congenital valve abnormality; primary disease of the heart muscle itself (cardiomyopathy); other defects in the heart present at birth (congenital heart disease); and infection of the heart valves and/or heart muscle itself (endocarditis and/or myocarditis). Each of these disease processes can lead to congestive heart failure.

Congestive heart failure is one of the most serious cardiovascular diseases affecting adults. Over 4 million people have congestive heart failure, and the incidence is on the rise. The incidence of this disease or condition is increasing with the aging of the population and is currently the most common cause for hospital admission in the elderly. The total U.S. healthcare expenditure on CHF is over five billion dollars per year.

Congestive heart failure results in systolic left ventricular dysfunction and sodium and water retention. This is most commonly due to myocardial infarction, but can also be due to pressure or volume overload, viral infection, an autoimmune process or direct toxins. After this initial insult, the disease often progresses due to poorly understood mechanisms. These mechanisms are believed to involve localized inflammatory responses involving nitric oxide release and its local production, COX-2 expression, immune mediators and inflammatory cytokines.

Current therapies for CHF are aimed at interrupting the systemic effects of CHF without addressing the myocardial process directly. There is now evidence that the progression of heart failure is mediated by inflammatory mechanisms. For example, cytokines and other inflammatory mediators have been shown to be elevated in CHF and are increased at the tissue level. In addition, matrix metalloproteinases, which are involved in many types of inflammatory and reparative responses are also involved in the adverse remodeling of the myocardium in CHF.

Consequently one object of the present invention is to treat or prevent heart disease by inhibiting the sequelae that are caused by COX-2 expression in the heart.

Another object of the present invention is to potentiate the effect of conventional agents that are used in the treatment or prevention of heart disease.

These and other objects will become obvious from the description provided herein.

SUMMARY OF THE INVENTION

A method of treating or preventing heart disease in a mammalian patient in need thereof is disclosed, comprising administering to said patient a COX-2 selective inhibiting compound in an amount that is effective to treat or prevent heart disease.

DESCRIPTION OF THE INVENTION

In one aspect of the invention, a method of treating or preventing heart disease in a mammalian patient in need thereof is disclosed, comprising administering to said patient a COX-2 selective inhibiting compound in an amount that is effective to treat or prevent heart disease.

In a more particular aspect of the invention, a method of treating or preventing congestive heart failure in a mammalian patient in need of such treatment or prevention is disclosed, comprising administering to said patient a COX-2 selective inhibiting compound in an amount that is effective to treat or prevent congestive heart failure.

More particularly, an aspect of the invention that is of interest relates to a method of treating or preventing congestive heart failure in a mammalian patient in need of such treatment or prevention, comprising administering to said patient a COX-2 selective inhibiting compound selected from the group consisting of: rofecoxib, MK-663, celecoxib, valdecoxib and parecoxib in an amount that is effective to treat or prevent heart disease.

Another aspect of the invention that is of particular interest relates to the method described above wherein the COX-2 selective inhibiting compound is administered to the patient along with at least one member selected from the group consisting of:

- digoxin, digitoxin, digitalis, dobutamine, dopamine, epinephrine, potassium chloride, calcium chloride, quinidine, lidocaine, tocainide, mexiletine, disopyramide, procainamide, phenytoin, flecainide, encainide, propafenone, indecainide, nitroglycerin, pentaerythritol, isosorbide, amiodarone, furosemide, torsemide, bumexinide, ethacrynic acid, spironolactone, triamterene, hydrochlorothiazine, amiloride, milrinone, amrinone,
- an angiotensin converting enzyme inhibitor, such as enalapril, captopril or lisinopril;
- a beta adrenergic blocking drug, such as carvedilol, atenolol or metoprolol,
- an alpha adrenergic blocking drugs, such as doxazocin, prazocin or alpha methyldopa,
- a calcium channel blocking agent such as amlodipine, nifedipine or verapamil; and
- an angiotensin II receptor antagonist, such as candesartan, irbesartan, losartan or valsartan.

Another method that is of particular interest relates to a method of treating or preventing congestive heart failure in a mammalian patient which comprises administering a COX-2 selective inhibitor in combination with an inotropic agent in an amount that is effective for treating or preventing congestive heart failure.

More particularly, a method that is of particular interest relates to a method treating or preventing congestive heart failure as described above wherein the inotropic agent is selected from the group consisting of: digoxin, digitoxin, digitalis, dobutamine, dopamine, epinephrine, milrinone, amrinone and norepinephrine.

Another method that is of particular interest relates to a method of treating or preventing congestive heart failure in a mammalian patient which comprises administering a COX-2 selective inhibitor in combination with an antihypertensive agent in an amount that is effective for treating or preventing congestive heart failure.

More particularly, the method described above is further defined wherein the antihypertensive agent is selected from: a diuretic, an angiotensin converting enzyme inhibitor, a calcium channel blocking drug and an β-adrenergic blocking drug.

The COX-2 inhibiting compound may be administered in combination with one or more conventional agents, e.g., α-adrenergic antagonist, angiotensin II antagonist, angiotensin converting enzyme inhibitor, β-adrenergic antagonist, antiarrhythmic agent, antihypertensive, atriopeptidase inhibitor (alone or with ANP), β-blocker, calcium channel blocker, diuretic, digitalis, phosphodiesterase inhibitor, renin inhibitor, sertonin antagonist, sympatholytic agent and/or a vasodialoator. For example, acetazolamide, altizide, amiloride, aminophylline, amrinone, azosemide, atenolol, atriopeptin, bendroflumethiazide, benzapril, benzclortriazide, benzthiazide, butizide, candesartan, captopril, ceranopril, chlorothalidone, chlorothiazide, cilazapril, cilexetil, clonidine, cromakalim, cryptenamine acetates and cryptenamine tannates, cyclopenthiazide, cyclothiazide, delapril, deserpidine, diazoxide, digitalis, digoxin, diflusinal, diltiazem, dopamine, dobutamine, doxazosin, enalapril, enalaprilat, eprosartan, ethacrynic acid, ethiazide, felodipine, fosinopril, furosemide, guanabenz, guanethidine, guanethidine sulfate, hydralazine hydrochloride, hydrochlorothiazide, hydroflumethiazide, idrapril, imidapril, irbesartan, isradipine, ketanserin, libenzapril, lisinopril, losartan, merethoxylline procaine, methylchlothiazide, metolazone, metoprolol, metoprolol tartate, methyclothiazide, methyldopa, methyldopate hydrochloride, milrinone, minoxidil, moexipril, moveltopril, nadolol, nicardipine, nifedipine, niludipine, nimodipine, nisoldipine, nitrendipine, nitroglycerine, nitroprusside, pargyline hydrochloride, penflutazide, pentopril, perindopril, pinacidil, pindolol, polythiazide, prazosin, prentyl, propranolol, quinapril, quinapril hydrochloride, quinethazone, ramapril, rauwolfia serpentina, rescinnamine, reserpine, sodium ethacrynate, sodium nitroprusside, spirapril, spironolactone, synecor, tasosartan, telmisartan, temocapril, teprotide, terazosin, ticrynafan, timolol maleate, triamterene, trichlormethazide, trandolopril, trichlormethiazide, trimethophan camsylate, utibapril, valsartan, verapamil, zabicipril, zalicipril, zofenopril, zofenopril calcium, zolasartan, and the like, as well as admixtures and combinations thereof.

Such compounds are known and normal daily dosages are well established. Typically, the individual daily dosages for these combinations may range from about one-fifth of the minimally recommended clinical dosages to the maximum recommended levels for the entities when they are given alone.

To illustrate these combinations, a COX-2 selective inhibitor administered at a clinically effective dosage, is given within the daily dose range and is effectively combined, at levels which are equal or less than the daily dose range, with the following compounds at the indicated per day dose range: hydrochlorothiazide (6–200 mg), chlorothiazide (125–2000 mg), furosemide (5–80 mg), ethacrynic acid (5–200 mg), amiloride (5–20 mg), diltiazem (30–540 mg), felodipine(1–60 mg), nifedipine(5–120 mg), nitrendipine(5–60 mg), timolol maleate (1–60 mg), propanolol (10–480 mg), an angiotensin II antagonist, such as losartan (2.5–250 mg, preferably 50 mg), and methyldopa (65–2000 mg).

In addition, triple drug combinations of a COX-2 selective inhibitor plus hydrochlorothiazide (15–200 mg), plus losartan (5–20 mg); or triple drug combinations of a COX-2 selective inhibitor, plus hydrochlorothiazide (15–200 mg), plus amiloride (5–20 mg); or triple drug combinations of a COX-2 selective inhibitor, plus hydrochlorothiazide (15–200 mg), plus timolol maleate (5–60 mg); or triple drug combinations of COX-2 selective inhibitor, plus hydrochlorothiazide (15–200 mg), plus nifedipine (5–60 mg) are effective combinations to control blood pressure in hypertensive patients. Similarly, quadruple drug combinations of a COX-2 selective inhibitor (1.0–200 mg), plus hydrochlorothiazide (15–200 mg), plus amiloride (5–20 mg), plus an angiotensin II antagonist (3–200 mg); or quadruple drug combinations of a COX-2 selective inhibitor (1.0–200 mg), plus hydrochlorothiazide (15–200 mg), plus timolol maleate (5–60 mg), plus an angiotensin II antagonist (0.5–250 mg); or quadruple drug combinations of a COX-2 selective inhibitor (1.0–200 mg), plus hydrochlorothiazide (15–200 mg), plus nifedipine (5–60 mg), plus an angiotensin II antagonist (0.5–250 mg) are also effective combinations to control blood pressure in hypertensive patients and/or provide benefit in the prevention or treatment of congestive heart failure. Naturally, these dose ranges may be adjusted on a unit basis as necessary to permit divided daily dosage and, as noted above, the dose will vary depending on the nature and severity of the disease, weight of patient, special diets and other factors.

A treatment that is of particular interest for CHF is a combination of digoxin, a diuretic, such as furosemide, an angiotensin converting enzyme inhibitor (ACE I) or angiotensin receptor blocker (ARB), a beta adrenergic blocking drug, such as metoprolol and a COX-2 selective inhibitor, such as rofecoxib, MK-663, celecoxib, valdecoxib or parecoxib.

The COX-2 selective inhibitor may be administered alone or in combination by oral, parenteral (e.g., intramuscular, intraperitoneal, intravenous or subcutaneous injection, or implant), nasal, vaginal, rectal, sublingual, or topical routes and can be formulated in dosage forms appropriate for each route of administration.

Solid dosage forms for oral administration include capsules, tablets, pills, powders and granules. In such solid dosage forms, the active compound is admixed with at least one inert pharmaceutically acceptable carrier such as sucrose, lactose or starch. Such dosage forms can also comprise, as is normal practice, additional substances other than inert diluents, e.g., lubricating agents such as magnesium stearate. Illustrative of the adjuvants which may be incorporated in tablets, capsules and the like are the following: a binder such as gum tragacanth, acacia, corn starch or gelatin; an excipient such as microcrystalline cellulose; a disintegrating agent such as corn starch, pregelatinized starch, alginic acid and the like; a lubricant such as magnesium stearate; a sweetening agent such as sucrose, lactose or saccharin; a flavoring agent such as peppermint, oil of wintergreen or cherry. In the case of capsules, tablets and pills, the dosage forms may also comprise buffering agents.

When the dosage form is a capsule, it may contain, in addition to materials of the above type, a liquid carrier such as fatty oil. Various other materials may be present as coatings or to otherwise modify the physical form of the dosage unit. Tablets and pills can additionally be prepared with enteric coatings and tablets may be coated with shellac, sugar or both.

Liquid dosage forms for oral administration include pharmaceutically acceptable emulsions, solutions, suspensions, syrups, the elixirs containing inert diluents commonly used in the art, such as water. Besides such inert diluents, compositions can also include adjuvants, such as wetting agents, emulsifying and suspending agents, and sweetening, flavoring, and perfuming agents. A syrup or elixir may contain the active compound, sucrose as a sweetening agent, methyl and propyl parabens as preservatives, a dye and a flavoring such as cherry or orange flavor.

Preparations according to this invention for parenteral administration include sterile aqueous or non-aqueous solutions, suspensions, or emulsions. Sterile compositions for injection may be formulated according to conventional pharmaceutical practice by dissolving or suspending the active substance in a vehicle such as water for injection, a naturally occurring vegetable oil like sesame oil, coconut oil, peanut oil, cottonseed oil, etc., or a synthetic fatty vehicle like ethyl oleate or the like. Buffers, preservatives, antioxidants and the like may be incorporated as required. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use. Compositions for rectal or vaginal administration are preferably suppositories which may contain, in addition to the active substance, excipients such as cocoa butter or a suppository wax. Compositions for nasal or sublingual administration are also prepared with standard excipients well known in the art.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease, the patient's weight, special diets then being followed by a patient, concurrent medication, and other factors which those skilled in the art will recognize. Based upon the foregoing, precise dosages are left to the discretion of the skilled clinician. Generally, dosage levels of between 0.0001 to 10 mg/kg. of body weight daily are administered to mammalian patients, e.g., humans. The dosage range will generally be about 0.5 mg to 1.0 g. per patient per day which may be administered in single or multiple doses. Perferably, the dosage range will be about 0.5 mg to 1000 mg per patient per day; more preferably about 0.5 mg to 200 mg per patient per day.

Methods of making COX-2 selective inhibitors are well understood from the patent literature. For example, compounds useful herein and methods of synthesis are disclosed in PCT WO95/00501 published on Jan. 5, 1995, U.S. Pat. No. 5,861,419 granted on Jan. 19, 1999, PCT WO97/14691 published on Apr. 24, 1997, U.S. Pat. No. 5,859,257 granted on Jan. 12, 1999 and PCT WO 97/38986. These publications are incorporated by reference. The compounds rofecoxib, MK-663. celecoxib, valdecoxib and parecoxib have known structures, as well as known dosages and dosage ranges. Utility for COX-2 selective inhibitors in treating heart disease is demonstrated as follows:

The effect of the COX-2 inhibiting compound is evaluated on the progression of heart failure in a known model in mice, except that a novel echocardiography method is employed using intravascular ultrasound (IVUS) catheters to achieve high resolution cardiac imaging in-vivo. The COX II-selective inhibitor slows the progression of the disease, as manifested by improved mortality and improvement in LV function and size.

Creation of Congestive Heart Failure

LV dysfunction was induced in 100 CD-1 mice with 6 weekly IP injections of 4 mg/kg doxorubicin. The mice were weighed and given a dose equal to 4mg/kg. This method of creating CHF in mice has been described in prior studies and is known to be reproducible, causing progression to end stage heart failure in the majority of animals. After the six week period, the mice exhibited signs of heart failure, such as edema and ascites. Deaths occurred as described below.

The Cyclooxygenase II Inhibitor

The dose of COX II inhibitor is equivalent to a relatively high therapeutic dose in humans, or approximately, 0.1 mg/gram per day. The drug was added to the feed of the animals on a daily basis.

Echocardiography

In vivo imaging of the mouse heart is difficult using conventional ultrasound probes, which utilize frequencies of less than 15 MHz and thus, have limited resolution in visualizing the small structures of the beating mouse heart. The non-invasive technique used accurately images the mouse heart in vivo using a 20 MHz intravascular ultrasound (IVUS) catheter (Boston Scientific 6F-20 MHz IVUS). The animal was given light anesthesia with ketamine and xylazine; the chest was shaved and mineral oil was applied to create an acoustic interface. The animal was placed on a warming blanket to avoid hypothermia and bradycardia. The IVUS catheter was placed with the transducer over the left sternal border and rotated in different orientations to obtain short and long axis LV images. A single observer measured the ejection fraction in 100 mice using this technique and obtained an average of 71 with a standard deviation of 4.8, indicating good reproducibility of the measurement technique.

Four serial measurements were performed over a 10 week period, indicating the ability of the technique to follow progression of disease and affect of treatment over time. The IVUS catheter has an axial resolution of 0.2 mm and a depth of penetration of over 15 mm, allowing visualization of the entire heart, the endocardium, epicardium and intra cardiac structures.

Treatment Protocol

The mice were split into two even groups, one to act as control, one to receive the COX-2 inhibitor. Echocardiography was performed at baseline and at intervals thereafter to follow changes in systolic function. The study scheme was as follows.

TABLE 1

Group 1 Control (n = 100)

| Day | Procedure |
|---|---|
| 1 | Sedation and Echocardiography, then doxorubicin 4 mg/kg IP |
| 7 | doxorubicin 4 mg/kg IP |
| 14 | doxorubicin 4 mg/kg IP |
| 28 | doxorubicin 4 mg/kg IP |
| 35 | doxorubicin 4 mg/kg IP |
| 42 | Sedation and Echocardiography |
| 56 | Sedation and Echocardiography |
| 70 | Sedation and Echocardiography |

TABLE 2

Group 2-COX-2* Group (n = 100)

| Day | Procedure |
|---|---|
| 1–70 | Same as in Control group, except that COX-2 inhibitor* is included in feed daily for days 42–70. |
| 70 | Sacrifice and assay for myocardial COX-2 expression and LV morphologic assessment |

*3-(3,4-Difluorophenyl)-4-[4-(methylsulfonyl)phenyl]-2,5-dihydro-2-furanone.

Repeated echocardiographic measures were performed by a trained observer blinded to the treatment group, and the data were analyzed using a Time Treatment interaction followed by pairwise comparisons adjusted using the Bonferroni correction. ANOVA confirmed a protective effect of the treatment on LV ejection fraction and shortening fraction (see Table 3 below).

TABLE 3

|  | Baseline | After doxorubicin | After 2 Weeks of treatment | After 4 weeks of treatment |
|---|---|---|---|---|
| Control LV Ejection Fraction | 72 | 60 | 52* | 51*/† |
| COX LV Ejection Fraction | 70 | 63 | 61* | 64*/† |
| Control LV Shortening Fraction | 27 | 22 | 21* | 20* |
| COX LV Shortening Fraction | 26 | 24 | 23* | 24* |

*p < .01 comparing each value to its control
†p < 0.01 comparing difference in change from baseline to end of treatment
‡LV means left ventricle During the treatment period the COX-2 inhibitor treated mice had an 18% mortality compared to 38% in the control group (p<0.01).

While the invention has been described with reference to certain particular embodiments thereof, those skilled in the art will appreciate that various modifications may be made without departing from the spirit and scope of the invention. The scope of the appended claims is not to be limited to the specific embodiments described.

What is claimed is:

1. A method of treating or preventing congestive heart failure in a mammalian patient, comprising administering to said patient a COX-2 selective inhibiting compound in an amount that is effective to treat or prevent congestive heart failure.

2. A method in accordance with claim 1 wherein the COX-2 selective inhibiting compound is selected from the group consisting of: rofecoxib, MK-663, celecoxib, valdecoxib and parecoxib.

3. A method in accordance with claim 1 further comprising administering to the patient a compound selected from the group consisting of: digoxin, digitoxin, digitalis, dobutamine, dopamine, epinephrine, quinidine, lidocaine, tocainide, mexiletine, disopyraminde, procainamide, phenytoin, flecainide, propafenone, nitroglycerin, pentaerythritol, isosorbide, amiodarone, furosemide, torsemide, bumetinide, ethacrynic acid, spironolactone, triamterene, hydrochlorothiazide, amiloride, milrinone, amrinone, angiotensin converting enzyme inhibitors, beta adrenergic blocking drugs, alpha adrenergic blocking drugs, calcium channel blocking agents, and angiotensin II receptor antagonists.

4. The method of claim 3, further defined as comprising administering to the patient an angiotensin converting enzyme inhibitor, wherein said angiotensin converting enzyme inhibitor is enalapril, captopril, lisinopril, trandolopril, or ramapril.

5. The method of claim 3, further defined as comprising administering to the patient a beta adrenergic blocking drug, wherein said adrenergic blocking drug is propranolol, atenolol, bisoprolol, carvedilol, metoprolol, or metoprolol tartate.

6. The method of claim 3, further defined as comprising administering to the patient an alpha adrenergic blocking drug, wherein said alpha adrenergic blocking drug is doxazocin, prazocin or alpha methyldopa.

7. The method of claim 3, further defined as comprising administering to the patient a calcium channel blocking agent, wherein said calcium channel blocking agent is amlodipine, nifedipine, verapamil, or diltiazem.

8. The method of claim 3, further defined as comprising administering to the patient an angiotensin II receptor antagonist, wherein said angiotensin II receptor antagonist is candesartan, irbesartan, losartan or valsartan.

9. The method of claim 1 wherein the mammal is a human.

10. A method of treating congestive heart failure in a mammal which comprises administering a therapeutically effective amount of a COX-2 selective inhibitor in combination with an antihypertensive agent.

11. The method of claim 10 wherein the antihypertensive agent is selected from: a diuretic, an angiotensin converting enzyme inhibitor, a calcium channel blocking drug and a β-adrenergic blocking drug.

12. A method of treating or preventing congestive heart failure in a mammalian patient, comprising administering to the patient a COX-2 selective inhibiting drug and an inotropic agent in an amount that is effective to treat or prevent congestive heart failure.

13. A method of treating or preventing congestive heart failure in a mammalian patient, comprising administering to the patient a COX-2 selective inhibiting drug, digoxin, a diuretic and a beta adrenergic blocking drug, said drugs being administered in an amount that is effective to treat or prevent congestive heart failure.

14. A method in accordance with claim 13 wherein the diuretic is furosemide.

15. A method in accordance with claim 13 wherein the beta adrenergic blocking drug is metoprolol.

16. A method in accordance with claim 14 wherein the COX-2 selective inhibiting drug is selected from the group consisting of: rofecoxib, MK-663, celecoxib, valdecoxib and parecoxib.

* * * * *